US009938306B2

(12) United States Patent
Qiu et al.

(10) Patent No.: US 9,938,306 B2
(45) Date of Patent: Apr. 10, 2018

(54) FLUOROALKYLSILANES AND COATINGS THEREFROM

(71) Applicant: 3M INNOVATIVE PROPERTIES COMPANY, St. Paul, MN (US)

(72) Inventors: Zai-Ming Qiu, Woodbury, MN (US); Jitendra S. Rathore, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 137 days.

(21) Appl. No.: 15/023,748

(22) PCT Filed: Sep. 23, 2014

(86) PCT No.: PCT/US2014/056865
§ 371 (c)(1),
(2) Date: Mar. 22, 2016

(87) PCT Pub. No.: WO2015/050740
PCT Pub. Date: Apr. 9, 2015

(65) Prior Publication Data
US 2016/0229875 A1   Aug. 11, 2016

Related U.S. Application Data

(60) Provisional application No. 61/886,842, filed on Oct. 4, 2013.

(51) Int. Cl.
*C07F 7/18* (2006.01)
*C08G 77/24* (2006.01)
*C09D 183/08* (2006.01)
*C09D 5/00* (2006.01)
*C08K 3/36* (2006.01)

(52) U.S. Cl.
CPC ............ *C07F 7/1836* (2013.01); *C07F 7/184* (2013.01); *C07F 7/1844* (2013.01); *C07F 7/1872* (2013.01); *C08G 77/24* (2013.01); *C09D 5/00* (2013.01); *C09D 183/08* (2013.01); *C08K 3/36* (2013.01)

(58) Field of Classification Search
None
See application file for complete search history.

(56) References Cited

U.S. PATENT DOCUMENTS

| | | | |
|---|---|---|---|
| 3,159,662 A | 12/1964 | Ashby |
| 3,178,464 A | 4/1965 | Pierpoint |
| 3,220,972 A | 11/1965 | Lamoreaux |
| 3,313,773 A | 4/1967 | Lamoreaux |
| 3,410,886 A | 11/1968 | Joy |
| 3,470,225 A | 9/1969 | Knorre |
| 3,484,470 A | 12/1969 | Pittman |
| 3,567,755 A | 3/1971 | Colgne |
| 3,715,334 A | 2/1973 | Karstedt |
| 3,775,452 A | 11/1973 | Karstedt |
| 3,814,730 A | 6/1974 | Karstedt |
| 3,814,731 A | 6/1974 | Nitzche |
| 4,276,252 A | 6/1981 | Kreis |
| 4,288,345 A | 9/1981 | Ashby |
| 4,510,094 A | 4/1985 | Drahnak |
| 4,530,879 A | 7/1985 | Drahnak |
| 4,603,215 A | 7/1986 | Chandra |
| 4,640,939 A | 2/1987 | Cavezzan |
| 4,670,531 A | 6/1987 | Eckberg |
| 4,699,813 A | 10/1987 | Cavezzan |
| 4,705,765 A | 11/1987 | Lewis |
| 4,712,092 A | 12/1987 | Boldridge, Jr. |
| 4,916,169 A | 4/1990 | Boardman |
| 5,082,706 A | 1/1992 | Tangney |
| 5,126,394 A | 6/1992 | Revis |
| 5,274,159 A | 12/1993 | Pellerite |
| 5,286,815 A | 2/1994 | Leir |
| 5,317,073 A | 5/1994 | Evans |
| 5,578,381 A | 11/1996 | Hamada |
| 5,639,845 A | 6/1997 | Inomata |
| 5,648,407 A | 7/1997 | Goetz |
| 5,677,050 A | 10/1997 | Bilkadi |

(Continued)

FOREIGN PATENT DOCUMENTS

| | | | |
|---|---|---|---|
| EP | 75865 A2 * | 4/1983 | ............... C07F 7/12 |
| EP | 0238033 | 9/1987 | |
| EP | 1 535 892 | 6/2005 | |
| GB | 2443626 | 5/2008 | |
| JP | 1-226844 | 9/1989 | |
| WO | WO 1998-40439 | 9/1998 | |
| WO | WO 2006-007917 | 1/2006 | |
| WO | WO 2010/009296 | 1/2010 | |
| WO | WO 2010-144352 | 12/2010 | |
| WO | WO 2014-099497 | 6/2014 | |
| WO | WO 2015-050928 | 4/2015 | |

OTHER PUBLICATIONS

Furukawa "Reactivity of Cyclosiloxane With 3,3,4,4,5,5,6,6,6-Nonafluorohexyl Group and Its Application to Fluorosilicone Synthesis", Journal of Applied Polymer Science, Dec. 20, 2001, vol. 82, No. 13, pp. 3333-3340.

Furukawa, "Synthesis and Properties of Fluorosilicone With Perfluorooctylundecyl Side Chains", Journal of Polymer Science Part A: Polymer Chemistry, Sep. 1, 2003, vol. 41, No. 17, pp. 2704-2714.

Kobayashi, "Surface Tension of Poly (3,3,4,4,5,5,6,6,6-nonafluorohexyl)-Methylsiloxane]", Macromolecules, 1990, vol. 23, pp. 4929-4933.

International Search Report for PCT International Application No. PCT/US2014/056865 dated Nov. 25, 2014, 3 pages.

*Primary Examiner* — Robert S Loewe
(74) *Attorney, Agent, or Firm* — Kent S. Kokko

(57) ABSTRACT

Novel fluoroalkysilanes of the following formula are described; $R_f$—O—CHFCF$_2$—O—(CH$_2$)$_n$—Si(R)$_x$X$_{3-x}$, wherein $R_f$ is a perfluoroalkyl group, optionally substituted by one or more in-chain -Q-, —S— or —NR$^{f1}$-heteroatoms, where $R_f^1$ is a -perfluoroalkyl; X is a hydrolysable group; R is a $C_1C_4$ alkyl group; n is at least 3; and x is 1 to 3.

15 Claims, No Drawings

(56) References Cited

U.S. PATENT DOCUMENTS

| | | | |
|---|---|---|---|
| 5,688,884 | A | 11/1997 | Baker |
| 6,129,980 | A | 10/2000 | Tsukada |
| 6,255,536 | B1 | 7/2001 | Worm |
| 6,299,799 | B1 | 10/2001 | Craig |
| 6,329,058 | B1 | 12/2001 | Arney |
| 6,353,037 | B1 | 3/2002 | Thunhorst |
| 6,376,569 | B1 | 4/2002 | Oxman |
| 6,462,100 | B1 | 10/2002 | Thunhorst |
| 6,479,610 | B1 | 11/2002 | Singh |
| 6,482,979 | B1 | 11/2002 | Hintzer |
| 6,646,088 | B2 | 11/2003 | Fan |
| 6,753,360 | B2 | 6/2004 | Mielewski |
| 6,803,109 | B2 | 10/2004 | Qiu |
| 7,056,846 | B2 | 6/2006 | Clark |
| 7,199,197 | B2 | 4/2007 | Caldwell |
| 7,279,210 | B2 | 10/2007 | Hulteen |
| 7,294,731 | B1 * | 11/2007 | Flynn .................... C07F 7/1836 556/427 |
| 7,407,710 | B2 | 8/2008 | Qiu |
| 7,410,704 | B2 | 8/2008 | Qiu |
| 7,413,807 | B2 | 8/2008 | Qiu |
| 7,893,186 | B2 | 2/2011 | Yang |
| 2005/0113609 | A1 | 5/2005 | Furukawa |
| 2011/0020657 | A1 | 1/2011 | Chang |
| 2012/0157703 | A1 | 6/2012 | Marciniec |
| 2012/0219794 | A1 | 8/2012 | Seth |

* cited by examiner

FLUOROALKYLSILANES AND COATINGS THEREFROM

CROSS REFERENCE TO RELATED APPLICATIONS

This application is a national stage filing under 35 U.S.C. 371 of PCT/US2014/056865, filed Sep. 23, 2014, which claims the benefit of U.S. Application No. 61/886,842, filed Oct. 4, 2013, the disclosure of which is incorporated by reference in its/their entirety herein.

FIELD

This invention relates to methods of treating substrates (especially substrates having a hard surface such as, for example, ceramics or glass) to impart water, oil, stain, and/or dirt repellency to a surface thereof, and, in other aspects, this invention relates to compositions for use in the methods and to substrates treated thereby.

BACKGROUND

Various fluorochemical compositions have been used as coating compositions for application to substrates (for example, hard surface substrates and fibrous substrates) to impart low surface energy characteristics such as oil and/or water repellency (oleophobicity and/or hydrophobicity). When used in coatings or films, however, many fluorochemical materials have tended to diffuse to the surface of the coating or film and to become depleted over time (for example, due to repeated cleanings of the surface). This has led to the use of fluorochemical derivatives having reactive or functional groups (for example, perfluoropolyether thiols, silanes, phosphates, and acrylates) to enable covalent attachment to the coatings, films, or substrate surfaces.

Silane compounds having one or more fluorochemical groups have been used (alone and in combination with other materials) to prepare surface treatment compositions for substrates such as glass and ceramics. Such silane compounds have typically included one or more hydrolyzable groups and at least one polyfluorinated alkyl or polyether group.

Numerous fluorochemical surface treatments have been developed and have varied in their ease of applicability to substrates (for example, due to differences in viscosity and/or in solvent solubilities, some treatments even requiring expensive vapor deposition or multiple application steps), in their requisite curing conditions (for example, some requiring relatively high curing temperatures for relatively long periods of time), in their repellency levels, in their ease of cleaning, in their degrees of optical clarity, and/or in their durability (for example, in their chemical resistance, abrasion resistance, and/or solvent resistance). Many have also been at least somewhat substrate-specific, requiring production of multiple compositions to ensure adhesion to different substrates.

SUMMARY

Thus, we recognize that there exists an ongoing need for surface treatment processes (and fluorochemical compositions for use therein) that can meet the performance requirements of a variety of different surface treatment applications. Such processes will preferably be simple, cost-effective, compatible with existing manufacturing methods, and/or capable of imparting repellency (preferably, durable, tailored repellency) to a variety of different substrates.

Briefly, in one aspect, this invention provides a novel fluoroalkylsilane. In another aspect this disclosure provides a coating composition comprising the fluoroalkylsilane with high water repellency, as measure by the receding water contact angle. In another aspect this disclosure provides a practical process for making the fluoroalkylsilane with unique space linkage group. In another aspect, this disclosure provide a surface treatment process which comprises (a) providing at least one substrate having at least one major surface; coating the surface with the coating composition, and curing the coating. In another aspect this disclosure provides the coated articles which have high water contact angles, especially receding water repellency.

DETAILED DESCRIPTION

This disclosure provides fluoroalkylsilanes of the formula:

$$R_f\text{—O—CHFCF}_2\text{—O—(CH}_2)_q\text{—Si(X)}_xR_{3-x}, \qquad \text{I}$$

wherein
$R_f$ is a perfluoroalkyl group, optionally substituted by one or more in-chain —O—, —S— or —$NR_f^1$-heteroatoms, where $R_f^1$ is a perfluoroalkyl, preferably a $C_1$-$C_6$ perfluoroalkyl;
X is a hydrolysable group;
R is an alkyl group or an aryl group;
q is at least 3; and
x is 1 to 3.

The $R_f$ groups may be linear or branched and of the formula: $C_nF_{2n+1}$—, where n is at least 1, preferably at least 3, more preferably 3-6; or may be $C_nF_{2n+1}$—(O—$C_mF_{2m}$)$_p$—, where n is at least 1, m is at least 2, and p may be a number from 1 to 10;
or $C_nF_{2n+1}N(C_oF_{2o+1})$—$C_mF_{2m}$—, where n is at least 1, o is at least 1 and m is at least 2. Preferably, each of the perfluoroalkyl or perfluoroalkylene groups (e.g. $C_nF_{2n+1}$—, $C_oF_{2o+1}$ or —$C_mF_{2m}$—) are selected from $C_3$-$C_6$.

It has been reported that certain perfluorooctyl-containing compounds ($C_8F_{17}$—) may tend to bio-accumulate in living organisms; this tendency has been cited as a potential concern regarding some fluorochemical compositions. For example, see U.S. Pat. No. 5,688,884 (Baker et al.). As a result, there is a desire for fluorine-containing compositions effective in providing desired functional properties, e.g., water- and oil-repellency, surfactant properties, etc. while eliminating more effectively from biological systems. However, it has also been asserted that only perfluoroalkyl groups of the formula $F(CF_2)_n$— have six or greater carbons have the self-alignment capability to achieve useful performance, while shorter chains, e.g. $C_4F_9$— lack the self-alignment necessary for good performance. See Phillips and Dettree, J. Col and Interface Sci., vol. 56(2), August 1976.

Therefore it remains a challenge to provide shorter chain perfluoroalkyl compositions that are less bioaccumulative, while maintain the requisite performance.

In some preferred embodiments, the present fluoroalkylsilane compounds and coating compositions provide the necessary performance even with the shorter $C_3$-$C_6$ perfluoroalkyl groups. Furthermore, the short chain perfluorocarboxylic acids (the presumed intermediate degradation products) are less toxic and less bioaccumulative than the longer chain ($C_8$) homologues. For these reasons, the $R_f$ groups is preferably selected from $C_3$-$C_6$ perfluoroalkyl (and/or perfluoroalkylene) groups.

In some preferred embodiments, n is at least 6, i.e at least a —$C_6H_{12}$— alkylene. It has been observed that excellent repellency is achieved when the spacer alkylene is at least six carbons, as measured by the receding contact angle.

The X groups can be the same or different and are capable of hydrolyzing, for example, in the presence of water, optionally under acidic or basic conditions, to produce groups capable of undergoing a condensation reaction (for example, hydroxysilyl groups). Desirably, each X is independently selected from hydroxyl, halogen, alkoxy, acyloxy, aryloxy, and combinations thereof; most desirably, each X is independently alkoxy). It will be appreciated that the X groups will hydrolyze in the presence of water or moisture, and some portion of the X groups may be hydrolyzed to —OH groups, which may then form siloxane linkages with each other or with hydroxyl-containing substrate surface via dehydration condensation reactions.

In some preferred embodiments, alkoxy is —$OR^3$, and acyloxy is —$OC(O)R^3$, wherein each $R^3$ is independently a lower alkyl group ($C_1$-$C_6$). For certain embodiments, $R^3$ is preferably $C_{1-6}$ alkyl and more preferably $C_{1-4}$ alkyl. $R^3$ can be a linear or branched alkyl group. In some preferred embodiments, aryloxy is —$OR^4$, wherein $R^4$ is aryl, optionally comprising one or more substituents independently selected $C_{1-4}$ alkyl. For certain embodiments, $R^4$ is preferably unsubstituted or substituted $C_{6-12}$ aryl.

Preferred fluoroalkylsilanes include those where Rf is a short ($C_1$-$C_6$) perfluoroalkyl and perfluoroalkoxyalkyl group, q is 6 or greater and X is selected from Cl, $OCH_3$, $OCH_2CH_3$, $OCH_2CH_2CH_3$ or $OCH(CH_3)_2$. The preferred $R_f$ is selected from $CF_3$, $CF_3CF_2$, n-$C_3F_7$ and $CF_3OCF_2CF_2$.

The compounds of Formula I may be prepared by hydrosilation of a fluorinated compound of the formula:

$$R_f\text{—O—CHFCF}_2\text{—O—(CH}_2)_{q-2}\text{CH=CH}_2 \quad \text{II}$$

with a hydrosilane of the formula:

$$\text{H—Si(X)}_x\text{R}_{3-x}, \quad \text{III}$$

in the presence of a hydrosilation catalyst, where
$R_f$ is a perfluoroalkyl group, optionally substituted by one or more in-chain —O—, —S— or —$NR_f^1$-heteroatoms, where $R_f^1$ is a perfluoroalkyl, preferably a $C_1$-$C_6$ perfluoroalkyl;
X is a hydrolysable group;
R is an alkyl group or an aryl group;
q is at least 3; and
x is 1 to 3.

Numerous patents teach the use of various complexes of cobalt, rhodium, nickel, palladium, or platinum as catalysts for hydrosilylation between a compound containing silicon-bonded hydrogen such as formula III and a compound containing terminal aliphatic unsaturation. For example, U.S. Pat. No. 4,288,345 (Ashby et al) discloses as a catalyst for hydrosilylation reactions a platinum-siloxane complex. Additional platinum-siloxane complexes are disclosed as catalysts for hydrosilylation reactions in U.S. Pat. Nos. 3,715,334, 3,775,452, and 3,814,730 (Karstedt et al). U.S. Pat. No. 3,470,225 (Knorre et al) discloses production of organic silicon compounds by addition of a compound containing silicon-bonded hydrogen to organic compounds containing at least one non-aromatic double or triple carbon-to-carbon bond using a platinum compound of the empirical formula $PtX_2(RCOCR'COR'')_2$ wherein X is halogen, R is alkyl, R' is hydrogen or alkyl, and R'' is alkyl or alkoxy.

The catalysts disclosed in the foregoing patents are characterized by their high catalytic activity. Other platinum complexes for accelerating the aforementioned thermally-activated addition reaction include: a platinacyclobutane complex having the formula $(PtCl_2C_3H_6)_2$ (U.S. Pat. No. 3,159,662, Ashby); a complex of a platinous salt and an olefin (U.S. Pat. No. 3,178,464, Pierpoint); a platinum-containing complex prepared by reacting chloroplatinic acid with an alcohol, ether, aldehyde, or mixtures thereof (U.S. Pat. No. 3,220,972, Lamoreaux); a platinum compound selected from trimethylplatinum iodide and hexamethyldiplatinum (U.S. Pat. No. 3,313,773, Lamoreaux); a hydrocarbyl or halohydrocarbyl nitrile-platinum (II) halide complex (U.S. Pat. No. 3,410,886, Joy); a hexamethyl-dipyridine-diplatinum iodide (U.S. Pat. No. 3,567,755, Seyfried et al); a platinum curing catalyst obtained from the reaction of chloroplatinic acid and a ketone having up to 15 carbon atoms (U.S. Pat. No. 3,814,731, Nitzsche et al); a platinum compound having the general formula $(R')PtX_2$ where R' is a cyclic hydrocarbon radical or substituted cyclic hydrocarbon radical having two aliphatic carbon-carbon double bonds, and X is a halogen or alkyl radical (U.S. Pat. No. 4,276,252, Kreis et al); platinum alkyne complexes (U.S. Pat. No. 4,603,215, Chandra et al.); platinum alkenylcyclohexene complexes (U.S. Pat. No. 4,699,813, Cavezzan); and a colloidal hydrosilylation catalyst provided by the reaction between a silicon hydride or a siloxane hydride and a platinum (0) or platinum (II) complex (U.S. Pat. No. 4,705,765, Lewis).

Although these platinum complexes and many others are useful as catalysts in processes for accelerating the hydrosilation, processes for promoting the ultraviolet or visible radiation-activated addition reaction between these compounds may be preferable in some instances. Platinum complexes that can be used to initiate ultraviolet radiation-activated hydrosilation reactions have been disclosed, e.g., platinum azo complexes (U.S. Pat. No. 4,670,531, Eckberg); ($\eta^4$-cyclooctadiene)diarylplatinum complexes (U.S. Pat. No. 4,530,879, Drahnak); and ($\eta^5$-cyclopentadienyl)trialkylplatinum complexes (U.S. Pat. No. 4,510,094, Drahnak). Other compositions that are curable by ultraviolet radiation include those described in U.S. Pat. Nos. 4,640,939 and 4,712,092 and in European Patent Application No. 0238033. U.S. Pat. No. 4,916,169 (Boardman et al) describes hydrosilylation reactions activated by visible radiation. U.S. Pat. No. 6,376,569 (Oxman et al.) describes a process for the actinic radiation-activated addition reaction of a compound containing silicon-bonded hydrogen with a compound containing aliphatic unsaturation, said addition being referred to as hydrosilylation, the improvement comprising using, as a platinum hydrosilylation catalyst, an ($\eta^5$-cyclopentadienyl)tri(σ-aliphatic)platinum complex, and, as a reaction accelerator, a free-radical photoinitiator capable of absorbing actinic radiation, i.e., light having a wavelength ranging from about 200 nm to about 800 nm. The process can also employ, as a sensitizer, a compound that absorbs actinic radiation, and that is capable of transferring energy to the aforementioned platinum complex or platinum complex/free-radical photoinitiator combination, such that the hydrosilylation reaction is initiated upon exposure to actinic radiation. The process is applicable both to the synthesis of low molecular weight compounds and to the curing of high molecular weight compounds, i.e., polymers.

The preferred hydrosilane of the formula III is selected from H—$SiCl_3$, H—$Si(OMe)_3$ and H—$Si(OCH_2CH_3)_3$.

The unsaturation fluoroalkyl compounds of Formula II, in turn, may be prepared by reaction of a compound of the formula:

$$R_f\text{—O—CF=CF}_2 \quad \text{IV}$$

with a compound of the formula:

$$H-O-(CH_2)_{q-2}CH=CH_2, \quad\quad V$$

in the presence of a base catalyst as described in US20050113609,
and where q and $R_f$ are as previously defined.

The perfluorovinyl ether of Formula IV, in turn, may be prepared by fluoride ion catalyzed addition of a perfluorinated acid fluoride to hexafluoropropylene oxide, followed by decarboxylation, according to the techniques describe in U.S. Pat. No. 6,255,536 (Worm et al.), incorporated herein by reference. Perfluorinated acid fluoride may be obtained from hexafluoropropene oxide by reaction with a metal fluoride. Alternatively, the perfluorinated acid fluorides may be prepared by electrochemical fluorination of alcohols, acids or esters as known in the art, for example as described in U.S. Pat. No. 6,482,979 (Hintzer et al.), incorporated herein by reference.

Commercial available perfluorovinyl ethers of Formula IV are, for example, $CF_3OCF=CF_2$, $CF_3CF_2CF_2OCF=CF_2$ and $CF_3OCF_2CF_2CF_2OCF=CF_2$.

Generally, the coating is formulated in a solvent or mixed solvents for easy use at the concentration of 0.01 to 50 wt %; preferably at 0.1 to 20%.

For crosslink or curing of the coating, moisture is needed, either by addition of limited water to the coating formulation or absorption of moisture from air after coating on substrates. To accelerate the curing, a acid or base catalyst may be optionally presented in the formulation.

In some embodiments, the coating composition may further comprise a crosslinking agent for the fluoroalkylsilane. A class of useful crosslinkers includes compounds that can be represented by the following general formula:

$$Si(X^1)_z R^2_{4-z} \quad\quad VI$$

wherein each $X^1$ is independently hydroxyl, a hydrolyzable group, or a combination thereof; each $R^2$ is independently a $C_1$-$C_4$ alkyl group; t is an integer of 1, 2, 3 or 4. Preferences for $X^1$ and $R^2$ include those set forth above for the X and R groups of Formula I. The crosslinkers can be included in the surface treatment composition in any of a wide range of amounts (for example, from about 1 to 20 weight percent), depending, for example, upon the particular application and the desired properties. Most preferred are tetralkoxysilanes, such as commercial available tetraethoxysilane, alone or in a mixture with trialkoxysilanes.

A variety of non-functional inorganic oxide particulate solutions or dispersions can be used in the coating composition. The particles are typically substantially spherical in shape and relatively uniform in size. The particles can have a substantially monodisperse size distribution or a polymodal distribution obtained by blending two or more substantially monodisperse distributions. The inorganic oxide particles are typically non-aggregated (substantially discrete), as aggregation can result in precipitation of the inorganic oxide particles or gelation of the composition.

The inorganic oxide particles are typically colloidal, having an average particle diameter of about 0.001 to about 0.2 micrometers, less than about 0.05 micrometers, and less than about 0.03 micrometers. These size ranges facilitate dispersion of the inorganic oxide particles into the coating composition with desirable surface properties and optical clarity. The average particle size of the inorganic oxide particles can be measured using transmission electron microscopy to count the number of inorganic oxide particles of a given diameter.

Inorganic oxide particles include colloidal silica, colloidal titania, colloidal alumina, colloidal zirconia, colloidal vanadia, colloidal chromia, colloidal iron oxide, colloidal antimony oxide, colloidal tin oxide, and mixtures thereof. The inorganic oxide particles can consist essentially of or consist of a single oxide such as silica, or can comprise a combination of oxides, such as silica and aluminum oxide, or a core of an oxide of one type (or a core of a material other than a metal oxide) on which is deposited an oxide of another type. Silica is a common inorganic particle for general applications.

The inorganic oxide particles are often provided in the form of a sol containing a colloidal dispersion of inorganic oxide particles in liquid media including water and isopropanol as solvent. The sol can be prepared using a variety of techniques and in a variety of forms including hydrosols (where water serves as the liquid medium), organosols (where organic liquids so serve), and mixed sols (where the liquid medium contains both water and an organic liquid), e.g., as described in U.S. Pat. No. 5,648,407 (Goetz et al.); U.S. Pat. No. 5,677,050 (Bilkadi et al.) and U.S. Pat. No. 6,299,799 (Craig et al.), the disclosure of which is incorporated by reference herein. Aqueous sols (e.g. of amorphous silica) can be employed. Sols generally contain at least 2 wt-%, at least 10 wt-%, at least 15 wt-%, at least 25 wt-%, and often at least 35 wt-% colloidal inorganic oxide particles based on the total weight of the fluorosilane in the coating formulation. The amount of colloidal inorganic oxide particle is typically no more than 50 wt-%. Most water is generally removed from the aqueous sols prior to formulating with fluorosilane to prevent premature hydrolysis for sufficient shelf life stability.

The coating composition can be prepared by mixing the inorganic oxide particle solution, and other optional ingredients with the curable fluorosilane composition. The resulting composition after applied to a substrate usually is dried to remove substantially all of the solvent and/or water from the formulation or generated during the silanol dehydration condensation reaction.

Some embodiments, partially surface-modified inorganic particles, preferably nanoparticles (having an average particle size of less than 100 nanometers) may be used. These particles and nanoparticles are prepared from colloidal materials from the group of silica, zinc oxide, titania, alumina, zirconia, vanadia, chromia, iron oxide, antimony oxide, tin oxide, other colloidal metal oxides, and mixtures thereof, modified such that the particles can be easily formulated or dispersed with fluorosilane formulation; these particles can comprise essentially a single oxide such as silica or can comprise u core of an oxide of one type (or a core of a material) on which is deposited the oxide of another type. The particles have an average particle diameter of 5 to about 1000 nm, preferably less than 100 nanometers, more preferably 10 to 50 nm. Average particle size can be measured using transmission electron microscopy to count the number of particles of a given diameter. Additional examples of suitable colloidal silicas are described in U.S. Pat. No. 5,126,394, incorporated herein by reference. Such particles are described in U.S. Pat. Nos. 6,353,037, and 6,462,100 (Thunhorst et al.), and U.S. Pat. No. 6,329,058 (Arney et al.) and are incorporated herein by reference. The fluorosilane of formula I may also been used for partial modification of inorganic particles.

The resulting curable coating composition can have a relatively long shelf life in the absence of moisture. The components of the composition can be in the form of relatively viscous liquids that can be used in the surface treatment process of the invention in neat form or, preferably, in admixture with commonly-used solvents (for example, alkyl esters, ketones, alkanes, alcohols, and the like, and mixtures thereof).

In some embodiments, the coating composition further includes at least one organic solvent that can dissolve or suspend at least about 0.1 percent by weight of the fluoroalkylsilane of Formula I and silicate components of Formula VI, based upon the total weight of the surface treatment composition. In some embodiments, it can be desirable that the solvent or mixture of solvents have a solubility for water of at least about 1 percent by weight, and for certain of these embodiments, a solubility for acid of at least about 5 percent by weight. When solvent is used, useful concentrations of the components can vary over a wide range (for example, from about 0.01 or 0.1 or 1 to about 90 weight percent), depending upon the solubility of the components, the application method utilized, the nature of the substrate, and the desired surface treatment characteristics.

Suitable organic solvents for use in the surface treatment composition include aliphatic alcohols such as, for example, methanol, ethanol, and isopropanol; ketones such as acetone and methyl ethyl ketone; esters such as ethyl acetate and methyl formate; ethers such as diethyl ether, diisopropyl ether, methyl t-butyl ether, and dipropylene glycol monomethyl ether (DPM); hydrocarbons solvents such as alkanes, for example, heptane, decane, and other paraffinic solvents; perfluorinated hydrocarbons such as perfluorohexane and perfluorooctane; fluorinated hydrocarbons, such as pentafluorobutane; hydrofluoroethers such as methyl perfluorobutyl ether and ethyl perfluorobutyl ether, and the like; and combinations thereof. Preferred solvents include aliphatic alcohols, perfluorinated hydrocarbons, fluorinated hydrocarbons, hydrofluoroethers, and combinations thereof (more preferably, aliphatic alcohols, hydrofluoroethers, and combinations thereof; most preferably, hydrofluoroethers and combinations thereof).

The coating composition may comprise:
a) 0.25 to 10 wt. % fluoroalkylsilane of Formula I;
b) 0 to 20 wt. % inorganic particular filer;
c) 0 to 20 wt. % a silane crosslinker;
d) 0 to 10 wt. % of an acid catalyst;
in an organic solvent.

The coating composition can be used as a fluorochemical surface treatment to impart a degree of hydrophobicity and/or oleophobicity to a variety of substrates. Substrates suitable for use in the process of the invention (and for preparing the surface-treated articles of the invention) include those having at least one surface comprising a material that is solid and preferably substantially inert to any coating solvent that is used. Preferably, the surface treatment can adhere to the substrate surface through chemical interactions, physical interactions, or a combination thereof (more preferably, a combination thereof).

Suitable substrates can comprise a single material or a combination of different materials and can be homogeneous or heterogeneous in nature. Useful heterogeneous substrates include coated substrates comprising a coating of a material (for example, a glass or a primer) borne on a physical support (for example, a polymeric film).

Useful substrates include those that comprise wood, glass, minerals (for example, both man-made ceramics such as concrete and naturally-occurring stones such as marble and the like), polymers (for example, polycarbonate, polyester, polyacrylate, and the like), metals (for example, copper, silver, aluminum, iron, chromium, stainless steel, nickel, and the like), metal alloys, metal compounds (for example, metal oxides and the like), leather, parchment, paper, textiles, painted surfaces, and combinations thereof. Preferred substrates include those having siliceous surfaces in either primed or unprimed form. Preferred substrates include glass, minerals, wood, metals, metal alloys, metal compounds, primed polymers, and combinations thereof (more preferably, glass, minerals, metals, metal alloys, metal compounds, primed polymers, and combinations thereof; most preferably, glass, minerals, and combinations thereof).

Typically the substrate will be chosen based in part on the desired optical and mechanical properties for the intended use. Such mechanical properties typically will include flexibility, dimensional stability and impact resistance. The substrate thickness typically also will depend on the intended use. For most applications, substrate thicknesses of less than about 0.5 mm are preferred, and more preferably about 0.02 to about 0.2 mm. Self-supporting polymeric films are preferred. The polymeric material can be formed into a film using conventional filmmaking techniques such as by extrusion and optional uniaxial or biaxial orientation of the extruded film. The substrate can be treated to improve adhesion between the substrate and the coating layer, e.g., chemical treatment, corona treatment such as air or nitrogen corona, plasma, flame, or actinic radiation. If desired, an optional tie layer or primer can be applied to the substrate and/or coating layer to increase the interlayer adhesion.

For best efficacy, the substrate has a surface with groups capable of forming covalent bonds to the silane groups (for example, hydroxyl groups). In some embodiments, the suitability of the surface of the substrate can be improved by deposition of a primer or by some other physical or chemical surface modification technique. Plasma deposition techniques can be used, if desired.

The coating composition can be applied separately or in combination (preferably, in combination) to at least a portion of at least one major surface of the substrate in essentially any manner (and with essentially any thickness) that can form a useful coating. Useful application methods include coating methods such as dip coating, spin coating, spray coating, wiping, roll coating, brushing, spreading, flow coating, and the like, and combinations thereof.

Typically, the coating composition can be coated on the substrate such that after an optional drying, a monolayer of the surface treatment composition results. Typically, such a monolayer can be from about 0.001 to about 1 micrometer thick (more typically, from about 0.001 to about 0.10 microns thick).

After application to the substrate, the coating can be cured by exposure to heat and/or moisture. Moisture cure can be effected at temperatures ranging from room temperature (for example, about 20° C.) up to about 80° C. or more. Moisture curing times can range from a few minutes (for example, at the higher temperatures) to hours (for example, at the lower temperatures).

For the preparation of a durable coating, sufficient water typically can be present to cause hydrolysis of the hydrolyzable groups described above, so that condensation to form siloxane (Si—O—Si) groups between the fluoroalkylsilanes of Formula I and also the substrate. The water can be, for example, present in the coating composition, adsorbed on the substrate surface, or in the ambient atmosphere. Typically, sufficient water can be present for the preparation of a durable coating if the coating method is carried out at room temperature in an atmosphere containing water (for example, an atmosphere having a relative humidity of about 30 percent to about 50 percent). Preferably, the coating composition can undergo chemical reaction with the surface of the substrate to form a durable coating through the formation of covalent bonds (including Si—O—Si groups).

Useful moisture curing catalysts for silane compounds are well-known in the art and include organic or inorganic acids (for example, acetic acid, propionic acid, butyric acid, valeric acid, maleic acid, stearic acid, hydrochloric acid, nitric acid, sulfuric acid, phosphoric acid, hydrochloric acid, and the like, and combinations thereof), metal carboxylates, metal acetylacetonate complexes, metal powders, peroxides, metal chlorides, organometallic compounds, and the like, and combinations thereof.

When used, the acid catalysts can be present in amounts ranging from about 0.01 to about 10 weight percent (preferably, from about 0.25 to about 10 weight percent; more preferably, from about 0.25 to about 5 weight percent), based upon the total weight of catalyst and surface treatment composition).

A substrate to be coated can typically be contacted with the coating composition at room temperature (typically from 20° C. to 30°. Alternatively, the coating composition can be applied to substrates that are preheated at a temperature of, for example, between 60° C. and 150° C. Following application of the surface treatment composition, the coated substrate can be dried and the resulting coating cured at ambient temperature (for example, about 20° C. to about 30° C. or elevated temperature (for example, at about 40° C. to about 150° C.) for a time sufficient for the curing to take place.

The cured coating may be described by the general formula:

$$[R_f^2SiO_{3/2}]_a[SiO_{4/2}]_b[RSiO_{3/2}]_c,$$

where
$R_f^2$ is $R_f$—O—CHFCF$_2$—O—(CH$_2$)$_q$— and the unit is derived from the fluoroalkylsilane of Formula I where subscript "x" is 3,
[SiO$_{4/2}$] are units derived from the crosslinking silanes of Formula VI where subscript "z" is 4; [RSiO$_{3/2}$] are units derived from the crosslinking silanes of Formula VI where subscript "z" is 3, and subscripts a, b and c are numbers corresponding to the weight percents of each unit. It will be appreciated that some siloxane bond formation will form with certain substrates The curable coating composition can be applied to articles comprising one or more of the above-described substrates and then cured to form surface treatments in the form of crosslinked hardcoats. The hardcoats can exhibit surface and/or bulk properties that can be tailored by varying the degree of crosslinking and by varying the natures and relative amounts of the particulate filler. The hardcoats (with their often outstanding durability, adhesion, and repellency properties) can be widely used for applications requiring durable low surface energy characteristics (for example, anti-graffiti coatings for signs, buildings, transportation vehicles, and the like; easily cleanable and/or anti-smudge coatings for glass, paper, clothes, metals, ceramic tiles, electronic devices, optical devices, and the like; mold release coatings for polymer or composite molding; and the like).

A useful hardcoat coating composition comprises:
a) 0.5 to 5 wt % fluoroalkylsilane of Formula I;
b) 1 to 10 wt % nanoparticle silica, and/or
c) 1 to 10 wt % silane crosslinker.

In general, the method of coating comprises providing a substrate, coating at least a portion of the substrate with the coating composition, optionally drying to remove water and/or solvent, and curing the coating. The resulting coating articles are both oleo- and hydrophobic. In some embodiments the coating exhibits a having a receding water contact angle of at least 80°, or at least 90°.

EXAMPLES

Materials

Allyl alcohol, 4-pemten-1-ol, 5-hexen-1-ol and 10-undecen-1-ol are obtained from Aldrich Chemical Company, Milwaukee, Wis.
3-Buten-1-ol was obtained from GFS Organic Chemicals, Inc., Columbus, Ohio.
9-Decen-1-ol was obtained from TCI America, Portland, Oreg.
CH$_3$OCH$_2$CH$_2$OCH$_3$ was obtained from GFS Organic Chemicals, Inc. Powell, Ohio.
Platinum-divinyltetramethyldisiloxane complex in xylene (2.1-2.4% Pt(0), was obtained from Gelest Inc., Morrisville, Pa.
H—Si(OMe)$_3$ and H—Si(OEt)$_3$ was obtained from purchased from Aldrich Chemical Company, Milwaukee, Wis.
H—SiMe(OMe)$_2$ was obtained from TCI America, Portland, Oreg.
H—SiMe$_2$(OEt), obtained from Alfa Aesar, Waltham, Mass.
Isopropyl alcohol (IPA), ethyly alcohol (EtOH) was obtained from EMD, Billerica, Mass.
HNO$_3$ was obtained from VWR International, Radnor, Pa.
C$_8$F$_{17}$(CH$_2$)$_2$Si(OEt)$_3$ (CFS-1), was obtained from, PCR Inc., Gainesville, Fla.
C$_6$F$_{13}$(CH$_2$)Si(OMe)$_3$ (CSF-2), was obtained from Gelest, Inc., Morrisville, Pa.
C$_4$F$_9$(CH$_2$)$_2$Si(OMe)$_3$ (CSF-3), was obtained from Gelest, Inc., Morrisville, Pa.
C$_4$F$_9$SO$_2$NMeC$_3$H$_6$Si(OMe)$_3$ (FC-4405, CSF-4), was obtained from 3M Company, St. Paul, Minn., and can be prepared as described in U.S. Pat. No. 5,274,159 (Pellerite et al.)
ECC-1000 (CSF-5), perfluoropolyether based disilane, was obtained from 3M Company, St. Paul, Minn. under trade designation "3M™ Easy Clean Coating ECC-1000".
HFE-7100 was obtained from 3M Company, St. Paul, Minn. under trade designation "3M™ Novec™ 7100 Engineered Fluid".
TEOS, Si(OCH$_2$CH$_3$)$_4$, was obtained from Aldrich Chemical Company, Milwaukee, Wis.
Test Methods
Method for Determining Contact Angle
Coated films prepared in Examples and Coated Examples described below were rinsed for 1 minute with hand agitation in an isopropanol (IPA) bath prior to water and hexadecane (HD) contact angles measurements. Measurements were made using a VCA-2500XE video contact angle analyzer (available from AST Products, Billerica, Mass.). Reported values are the average of at least 3 drops; each drop was measured twice. Drop volumes were 5 µL for static measurements and 1-3 µL for advancing and receding.
Method for Testing Marker Repellency
Example and Comparative Example samples were tested for their marker repellency using a black marker (black, Sanford Sharpie pen with Super Permanent Ink, available from Sanford Corp., Keysborough, Australia). A straight line was drawn on the coated sample and a repellency rating was assigned to the coated sample based on the appearance of the line; "No" meant that the coated sample was not repellent, i.e., the line was continuous; "Some" meant that the coated sample was somewhat repellent, i.e., the line was beaded-up with broken line; "Good" meant that the coated sample was repellent, but with some limited continuous lines; "Excellent" meant that the coated sample was repellent, with no continuous lines visible.

Method for Testing Coating Durability

The durability of the coatings was determined by rubbing the sample surfaces (i.e., the coatings) using an abrasive Model 5900 TABER Reciprocating Abrasive apparatus with Crockmeter Standard Rubbing Cloth. The samples were rubbed at a speed of 75 cycles/minute, with an applied force of 13.6N. Samples were scratched for 50 cycles or 100 cycles and then their water and HD contact angles and marker repellency were determined to assess the durability of the coatings.

Preparation of Fluorinated Silanes

Fluorinated silanes (FS) according to the invention were made in a two-step process. First, fluoroalkenes, $R_f$—OCFHCF$_2$O(CH$_2$)$_{n-2}$—CH=CH$_2$, were prepared using procedures disclosed in the US Patent Publication, US2005/0313609, except using CH$_3$OCH$_2$CH$_2$OCH$_3$ as the solvent and with 5% excess of $R_f$—OCF=CF$_2$ according to the reaction

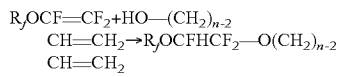

The reaction led to high yields of fluorinated alkenes (80~95%) which were subsequently isolated by distillation. Exemplary fluorinated alkenes produced as described above are listed below along with their boiling points (b.p.).

C$_3$F$_7$OCHFCF$_2$OCH$_2$CH=CH$_2$, b.p. 112-115° C.;
C$_3$F$_7$OCHFCF$_2$O(CH$_2$)CH=CH$_2$, b.p. 136-139° C.;
C$_3$F$_7$OCHFCF$_2$O(CH$_2$)$_3$CH=CH$_2$, b.p. 70-72.5° C./39 mmHg;
C$_3$F$_7$OCHFCF$_2$O(CH$_2$)$_4$CH=CH$_2$, b.p. 93-94° C./26 mmHg;
C$_3$F$_7$OCHFCF$_2$O(CH$_2$)$_8$CH=CH$_2$, b.p. 95-97° C./5.3 mmHg;
C$_3$F$_7$OCHFCF$_2$O(CH$_2$)$_9$CH=CH$_2$, b.p. 101-103° C./3.2 mmHg;
CF$_3$O(CF$_2$)$_3$OCHFCF$_2$O(CH$_2$)$_2$CH=CH$_2$, b.p. 151-154° C.;
CF$_3$O(CF$_2$)$_3$OCHFCF$_2$O(CH$_2$)$_4$CH=CH$_2$, b.p. 9294° C./26 mmHg;
C$_3$F$_7$OCF(CF$_3$)CF$_2$OCHFCF$_2$O(CH$_2$)$_2$CH=CH$_2$, b.p. 7578° C./16 mmHg

Then, the fluorosilanes, $R_f$—OCFHCF$_2$O(CH$_2$)$_n$—Si(OR)$_3$ were made by hydrosilylation of $R_f$—OCFHCF$_2$O(CH$_2$)n-CH=CH$_2$ with slightly excess of H—Si(OR)$_3$ (1:1.1 mole ratio) at room temperature in the presence of Pt(0) catalyst (40 ppm) under nitrogen according to the reaction

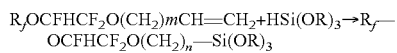

All of the R$_f$OCFHCF$_2$O(CH$_2$)n-CH=CH$_2$ prepared above (with the exception of C$_4$F$_9$—CH=CH$_2$) showed high reactivity to H—Si(OR)$_3$ (R=Me, Et), and the hydrosilation reactions were completed in 10 minutes to 2 hours at room temperature, as monitored by FT-IR and $^1$H NMR analyses. The formed silanes were isolated by distillation and the isolated yields from the distillation were ≥90%. The yield for the reaction of C$_4$F$_9$—CH=CH$_2$ was <5%. Exemplary fluorinated silanes produced as described above are listed below along with their boiling points (b.p.).

C$_3$F$_7$OCHFCF$_2$O(CH$_2$)$_3$Si(OEt)$_3$   b.p.=95-100° C./5.9 mmHg
C$_3$F$_7$OCHFCF$_2$O(CH$_2$)$_3$SiMe(OMe)$_2$   b.p.=96-100° C./16 mmHg
C$_3$F$_7$OCHFCF$_2$O(CH$_2$)$_3$SiMe$_2$(OEt)   b.p.=95-101° C./20 mmHg
C$_3$F$_7$OCHFCF$_2$O(CH$_2$)$_4$Si(OMe)$_3$   b.p.=80-83° C./1.7 mmHg
C$_3$F$_7$OCHFCF$_2$O(CH$_2$)$_4$Si(OEt)$_3$   b.p.=97-100° C./2.2 mmHg
C$_3$F$_7$OCHFCF$_2$O(CH$_2$)$_5$Si(OMe)$_3$   b.p.=103-104° C./4.2 mmHg
C$_3$F$_7$OCHFCF$_2$(CH$_2$)$_6$Si(OMe)$_3$   b.p.=99-102° C./1.8 mmHg
C$_3$F$_7$OCHFCF$_2$(CH$_2$)$_{10}$Si(OMe)$_3$   b.p.=135-136° C./2.1 mmHg
C$_3$F$_7$OCHFCF$_2$O(CH$_2$)$_{11}$Si(OEt)$_3$   b.p. 148-152° C./1.8 mmHg

General Method for Preparing Coating Solutions and Coating

Example and Comparative Example coating solutions were formulated by direct dilution of respective fluorinated silanes listed below in a desired solvent to 2 wt %. Then, 0.1 wt % of 0.1N nitric acid aqueous solution was added to the solution and the solutions were aged for at least 10 minutes before coating. Glass microscope slides (obtained from VWR International, Radnor, Pa.) were coated with coating solutions by dipping them into the solution. The resulting coatings were then cured al desired temperature for desired length of time before testing.

CFS-1, C$_8$F$_{17}$(CH$_2$)$_2$Si(OEt)$_3$
CSF-2, C$_6$F$_{13}$(CH$_2$)$_2$Si(OMe)$_3$
CSF-3, C$_4$F$_9$(CH$_2$)$_2$Si(OMe)$_3$
CSF-4, C$_4$F$_9$SO$_2$NMeC$_3$H$_6$Si(OMe)$_3$ (FC-4405)
CSF-5, ECC-1000, 0.1 wt % in HFE-7100
FS-1, C$_3$F$_7$OCHFCF$_2$O(CH$_2$)$_3$Si(OMe)$_3$
FS-2, C$_3$F$_7$OCHFCF$_2$O(CH$_2$)$_4$Si(OEt)$_3$
FS-3, C$_3$F$_7$OCHFCF$_2$(CH$_2$)$_6$Si(OMe)$_3$
FS-4, C$_3$F$_7$OCHFCF$_2$(CH$_2$)$_{10}$Si(OMe)$_3$
FS-5, C$_3$F$_7$OCHFCF$_2$O(CH$_2$)$_{11}$Si(OEt)$_3$

Examples 1-7 (EX1-EX7) and Comparative Examples 1-5 (CE1-CE5)

EX1-7 and CE1-CE5 samples were prepared using the general method for preparing coating solutions and coating described above. The resulting coated glass slides were dried at room temperature for 2 minutes and then in an oven at 110° C. for 2 minutes. Then, the water and hexadecane contact angle measurements were done for EX1-EX7 and CE1-CE5 samples using the methods described above. The composition of the coating solutions (i.e., the fluorosilane and the solvent used) as well as the contact angle data are summarized below in Table 1. Note that multiple samples for a given Example (e.g., EX3a, EX3b, etc.) denote that replicate samples were prepared and tested for a given Example.

TABLE 1

| Example | Coating Composition (Fluorosilane, wt % in solvent) | Water Contact Angle (degrees) | | | | | | Hexadecane Contact Angle (degrees) | | | | | |
|---|---|---|---|---|---|---|---|---|---|---|---|---|---|
| | | Advancing | | Receding | | Static | | Advancing | | Receding | | Static | |
| | | Left | Right | Left | Right | Left | Right | Left | Right | Left | Right | Left | Right |
| CE1 | CSF-1, 2% in IPA | 110.7 | 110.7 | 67.7 | 67.7 | 106.6 | 106.6 | 61.3 | 59.9 | 25.6 | 25.6 | 50.6 | 51.2 |
| CE2 | CSF-2, 2% in IPA | 110.8 | 110.8 | 70.2 | 69.7 | 107.6 | 107.2 | 65.0 | 65.0 | 27.9 | 27.9 | 60.8 | 60.8 |
| CE3 | CSF-3, 2% in IPA | 103.6 | 103.1 | 72.6 | 73.0 | 97.6 | 97.6 | 68.7 | 67.8 | 44.6 | 44.6 | 58.4 | 58.4 |
| CE4 | CSF-4, 2% in IPA | 116.3 | 116.3 | 79.8 | 79.8 | 107.1 | 107.1 | 79.5 | 79.5 | 53.4 | 53.4 | 63.2 | 63.2 |
| CE5 | CSF-5, 0.1% in HFE 7100 | 108.9 | 108.9 | 87.5 | 86.9 | 104.7 | 104.7 | 73.1 | 73.4 | 43.2 | 43.2 | 66.2 | 66.2 |
| EX1 | FS-1, 2% in IPA | 89.6 | 89.6 | 73.6 | 73.6 | 81.6 | 81.6 | 51.2 | 51.2 | 40.6 | 40.6 | 47.1 | 47.1 |
| EX2 | FS-2, 2% in IPA | 99.3 | 100.7 | 82.8 | 82.8 | 96.3 | 95.2 | 61.9 | 61.9 | 46.9 | 46.9 | 51.7 | 52.2 |
| EX3a | FS-3, 2% in IPA | 106.5 | 107.1 | 90.3 | 90.7 | 100.2 | 100.5 | 63.4 | 63.3 | 51.0 | 50.9 | 58.0 | 58.0 |
| EX3b | FS-3, 2% in IPA | 106.3 | 106.3 | 92.0 | 92.8 | 101.6 | 101.2 | 64.5 | 64.5 | 54.3 | 54.3 | 59.3 | 59.3 |
| EX3c | FS-3, 2% in IPA | 107.4 | 107.4 | 93.0 | 92.2 | 99.0 | 99.1 | 63.3 | 63.3 | 50.6 | 50.6 | 58.7 | 58.7 |
| EX4a | FS-4, 2% in IPA | 109.3 | 109.3 | 95.4 | 95.4 | 104.6 | 105.0 | 57.7 | 57.7 | 42.3 | 42.3 | 64.5 | 64.5 |
| EX4b | FS-4, 2% in IPA | 107.8 | 107.8 | 96.1 | 96.1 | 106.1 | 105.3 | 60.0 | 60.0 | 41.7 | 41.7 | 67.7 | 67.7 |
| EX5a | FS-5, 2% in IPA | 106.5 | 106.5 | 95.7 | 95.7 | 102.0 | 102.0 | 68.4 | 68.4 | 55.1 | 55.1 | 64.9 | 64.9 |
| EX5b | FS-5, 2% in IPA | 111.3 | 111.13 | 93.4 | 93.4 | 102.9 | 104.3 | 68.7 | 68.7 | 55.7 | 55.2 | 63.1 | 64.0 |
| EX6a | FS-4, 2% in EtOH | 109.2 | 109.2 | 95.2 | 95.2 | 103.5 | 103.5 | 74.4 | 74.4 | 49.3 | 49.3 | 61.0 | 61.0 |
| EX6b | FS-4, 2% in EtOH | 109.9 | 109.9 | 93.7 | 93.7 | 106.3 | 106.3 | 74.0 | 74.0 | 46.9 | 46.9 | 65.7 | 65.7 |
| EX6c | FS-4, 2% in EtOH | 109.5 | 109.5 | 96.3 | 96.3 | 102.8 | 102.8 | 75.1 | 75.1 | 48.5 | 48.5 | 64.8 | 64.8 |
| EX6d | FS-4, 2% in EtOH | 110.7 | 110.7 | 95.3 | 95.3 | 105.4 | 105.4 | 75.6 | 75.6 | 48.1 | 48.1 | 62.3 | 62.3 |
| EX7a | FS-5, 2% in EtOH | 108.9 | 108.9 | 93.7 | 93.7 | 103.5 | 103.5 | 71.6 | 71.6 | 43.1 | 43.1 | 65.4 | 65.4 |
| EX7b | FS-5, 2% in EtOH | 108.7 | 108.7 | 95.1 | 95.1 | 103.8 | 103.8 | 71.3 | 71.3 | 44.5 | 44.5 | 64.8 | 64.8 |
| EX7c | FS-5, 2% in EtOH | 109.1 | 109.1 | 93.4 | 92.2 | 104.2 | 104.2 | 73.5 | 73.5 | 44.8 | 44.8 | 67.9 | 67.9 |
| EX7d | FS-5, 2% in EtOH | 111.3 | 111.3 | 93.7 | 93.7 | 106.2 | 106.2 | 75.0 | 75.0 | 45.1 | 45.1 | 69.2 | 69.2 |

The marker repellency of the EX1-EX7 and CE3-CE5 samples were determined as described above. The results are summarized below in Table 2.

TABLE 2

| Example | Marker Repellency |
|---|---|
| CE3 | No |
| CE4 | Some |
| CE5 | Good |
| EX1 | No |
| EX2 | Some |
| EX3 | Excellent |
| EX4 | Excellent |
| EX5 | Excellent |
| EX6 | Excellent |
| EX7 | Excellent |

The durability of the EX3-EX5 and CE3 samples were determined as described above after subjecting them to 50 or 100 cycles of abrasive rubbing. The results are summarized below in Table 3.

TABLE 3

| Example | Abrasive cycles | Marker Repellency | Water Contact Angle (degrees) | | | | | |
|---|---|---|---|---|---|---|---|---|
| | | | Advancing | | Receding | | Static | |
| | | | Left | Right | Left | Right | Left | Right |
| CE3 | 50 | No | 79.3 | 79.3 | 41.2 | 41.2 | 77.8 | 77.8 |
| EX3a | 50 | | 100.8 | 100.8 | 85.2 | 85.2 | 91.3 | 91.3 |
| EX4a | 50 | | 106.6 | 106.6 | 95.1 | 95.1 | 100.9 | 100.9 |
| EX4a | 100 | | 106.4 | 106.4 | 93.7 | 93.7 | 104.5 | 104.5 |
| EX5a | 50 | | 106.0 | 106.0 | 91.2 | 91.2 | 98.6 | 98.6 |
| EX5a | 100 | | 104.9 | 104.9 | 89.5 | 89.5 | 97.6 | 97.6 |
| EX5b | 50 | | 106.9 | 106.9 | 90.9 | 90.9 | 96.6 | 96.6 |
| EX5b | 100 | | 106.0 | 106.0 | 88.5 | 88.5 | 93.2 | 93.2 |

Examples 8-9 (EX8-EX9) and Comparative Example 6 (CE6)

EX8 samples were prepared in the same manner as EX3. EX9 samples were prepared in the same manner as EX3, except that the coated glass slides were dried at room temperature for 24 hours. CE6 was prepared in the same manner as CB5, except that the coated glass slides were dried at room temperature (RT) for 24 hours. EX8-EX9 and CE6 samples were tested for their water and HD contact angles. The data is summarized below in Table 4.

TABLE 4

| | Water Contact Angle (degrees) | | | | | | Hexadecane Contact Angle (degrees) | | | | | |
|---|---|---|---|---|---|---|---|---|---|---|---|---|
| | Advancing | | Receding | | Static | | Advancing | | Receding | | Static | |
| Example | Left | Right | Left | Right | Left | Right | Left | Right | Left | Right | Left | Right |
| EX8a | 106.8 | 107.4 | 92.7 | 91.8 | 99.5 | 99.5 | 65.3 | 65.3 | 50.9 | 50.9 | 57.8 | 57.8 |
| EX8b | 106.1 | 106.1 | 92.0 | 92.0 | 97.3 | 97.3 | 64.6 | 64.6 | 49.6 | 49.6 | 57.1 | 57.1 |
| EX9a | 106.6 | 106.6 | 91.9 | 91.9 | 99.8 | 99.8 | 65.5 | 65.5 | 45.9 | 45.9 | 58.6 | 58.6 |
| EX9b | 107.9 | 107.9 | 93.2 | 93.0 | 98.0 | 98.0 | 66.4 | 66.4 | 44.2 | 44.2 | 61.8 | 61.8 |
| CE6 | 108.5 | 109.6 | 72.6 | 72.4 | 102.5 | 102.5 | 79.8 | 79.7 | 55.1 | 56.0 | 66.1 | 66.1 |

Example 10 (EX10) and Comparative Example 7 (CE7)

EX10 and CE7 samples were prepared in the same manner as EX5 and CE5, respectively, except that the coating compositions did not include the addition of 0.1N nitric acid. EX10 and CE7 samples were tested for their water and HD contact angles. The data is summarized below in Table 5.

TABLE 5

| | Water Contact Angle (degrees) | | | | | | Hexadecane Contact Angle (degrees) | | | | | |
|---|---|---|---|---|---|---|---|---|---|---|---|---|
| | Advancing | | Receding | | Static | | Advancing | | Receding | | Static | |
| Example | Left | Right | Left | Right | Left | Right | Left | Right | Left | Right | Left | Right |
| EX10a | 111.3 | 111.3 | 93.4 | 93.4 | 102.9 | 104.3 | 68.7 | 68.7 | 55.7 | 55.2 | 63.1 | 64.0 |
| EX10b | 106.5 | 106.5 | 95.7 | 95.7 | 102.0 | 102.0 | 68.4 | 68.4 | 55.1 | 55.1 | 64.9 | 64.9 |
| CE7 | 108.9 | 108.9 | 87.5 | 86.9 | 104.7 | 104.7 | 73.1 | 73.4 | 43.2 | 43.2 | 66.2 | 66.2 |

Examples 11-13 (EX10-EX13)

EX11-EX13 samples were prepared in the same manner as EX5, except that the concentration of the fluorosilane in the coating compositions was 1 wt %, 0.5 wt %, and 0.25 wt %, respectively. EX11-EX13 samples were tested for their water and HD contact angles. The data is summarized below in Table 6.

TABLE 6

| | Water Contact Angle (degrees) | | | | | | Hexadecane Contact Angle (degrees) | | | | | |
|---|---|---|---|---|---|---|---|---|---|---|---|---|
| | Advancing | | Receding | | Static | | Advancing | | Receding | | Static | |
| Example | Left | Right | Left | Right | Left | Right | Left | Right | Left | Right | Left | Right |
| EX11a | 107.9 | 107.9 | 91.0 | 91.0 | 99.7 | 99.7 | 66.3 | 66.3 | 41.2 | 41.2 | 62.4 | 62.4 |
| EX11b | 107.0 | 107.0 | 90.2 | 89.7 | 98.2 | 98.2 | 66.0 | 66.0 | 41.8 | 42.1 | 62.0 | 62.0 |
| EX12a | 101.3 | 101.3 | 89.8 | 90.7 | 96.4 | 96.6 | 67.4 | 67.4 | 39.8 | 40.2 | 61.3 | 61.3 |
| EX12b | 101.4 | 101.4 | 90.0 | 89.8 | 95.8 | 95.3 | 68.5 | 68.5 | 40.5 | 40.5 | 61.3 | 61.3 |
| EX13a | 91.7 | 91.7 | 78.9 | 78.9 | 80.3 | 81.7 | 62.6 | 62.6 | 33.9 | 33.9 | 51.8 | 51.8 |
| EX13b | 91.2 | 91.2 | 76.7 | 76.7 | 80.0 | 80.0 | 64.1 | 64.3 | 34.7 | 34.7 | 53.5 | 53.5 |

Examples 14-15 (EX14-EX15) and Comparative Examples 8-9 (CE8-CE9)

EX14-EX15 and CE8-CE9 samples were prepared in the same manner as EX2, EX3, CE2, and CE4, respectively, except that the coating compositions further included TEOS. The relative amount of the TEOS to the corresponding fluorosilanes was 30 wt % TEOS to 70 wt % fluorosilane. TEOS and fluorosilane, collectively, were diluted to 2 wt % in IPA. EX14-EX15 and CE8-CE9 samples were tested for their water and HD contact angles. The data is summarized below in Table 7.

TABLE 7

| Example | Water Contact Angle (degrees) | | | | | | Hexadecane Contact Angle (degrees) | | | | | |
|---|---|---|---|---|---|---|---|---|---|---|---|---|
| | Advancing | | Receding | | Static | | Advancing | | Receding | | Static | |
| | Left | Right | Left | Right | Left | Right | Left | Right | Left | Right | Left | Right |
| CE8 | 108.7 | 108.7 | 92.0 | 92.0 | 103.6 | 103.6 | 70.7 | 70.5 | 58.7 | 58.7 | 63.8 | 63.8 |
| CE9 | 119.8 | 119.8 | 63.5 | 63.5 | 103.0 | 102.2 | 108.4 | 108.4 | 39.5 | 39.5 | 62.0 | 61.4 |
| EX14 | 109.8 | 109.8 | 84.1 | 84.1 | 98.4 | 98.4 | 69.1 | 68.3 | 52.1 | 52.1 | 58.6 | 58.6 |
| EX15 | 106.5 | 106.5 | 93.4 | 93.4 | 100.3 | 100.3 | 68.9 | 68.9 | 51.7 | 51.7 | 63.5 | 63.5 |

This disclosure provides the following illustrative embodiments:

1. A fluoroalkylsilane of the formula:
   $R_f$—O—CHFCF$_2$—O—(CH$_2$)$_q$—Si(X)$_x$R$_{3-x}$, wherein
   $R_f$ is a perfluoroalkyl group, optionally substituted by one or more in-chain —O—, —S— or NR$_f^1$-heteroatoms, where R$_f^1$ is a perfluoroalkyl;
   X is a hydrolysable group;
   R is a C$_1$-C$_4$ alkyl group;
   q is at least 3; and
   x is 1 to 3.
2. The fluoroalkylsilane of embodiment 1 wherein $R_f$ is a C$_1$-C$_6$ perfluoroalkyl group.
3. The fluoroalkylsilane of any of the previous embodiments wherein X is selected from alkoxy, acetoxy and halide.
4. The fluoroalkylsilane of any of the previous embodiments wherein q is at least 6.
5. The fluoroalkylsilane of any of embodiments 1, 3 or 4 wherein $R_f$ is of the formula C$_n$F$_{2n+1}$—(O—C$_m$F$_{2m}$)$_p$—, where n is at least 1, m is at least 2, and p may be zero or a number from 1 to 10.
6. The fluoroalkylsilane of embodiment 5 wherein each of subscripts n and m are 3 to 6.
7. The fluoroalkylsilane of any of embodiments 1, 3 or 4 wherein $R_f$ is of the formula C$_n$F$_{2n+1}$N(C$_{2o}$F$_{2o+1}$)—C$_m$F$_{2m}$—, where n is at least 1, o is at least 1 and m is at least 2.
8. The fluoroalkylsilane of embodiment 7 wherein each of subscripts n, and m are 3 to 6.
9. The fluoroalkylsilane of any of embodiments 1, 3 or 4 where $R_f$ is selected from CF$_3$, C$_2$F$_5$, C$_3$F$_7$ and CF$_3$O(CF$_2$)$_3$; q is 6 and greater and X is selected from Cl, OCH$_3$, OCH$_2$CH$_3$, OCH$_2$CH$_2$CH$_3$ and OCH(CH$_3$)$_2$.
10. A coating composition comprising the fluoroalkyl silane of any of embodiments 1-9, a solvent and optional acid catalyst and optional inorganic oxide particulate filler.
11. The coating composition of embodiment 10, wherein the particulate filler is silica.
12. The coating composition of embodiment 11 wherein the silica is nanoparticle silica.
13. The coating composition of any of embodiments 11 or 12 wherein the silica is surface modified.
14. The coating composition of any of embodiments 11-13 further comprising one or more silane crosslinkers of the formula:
   Si(X$^1$)$_z$R$^2_{4-z}$
   wherein each X$^1$ is independently hydroxyl, a hydrolyzable group, or a combination thereof; each R$^2$ is independently a C$_1$-C$_4$ alkyl group; z is an integer of one to four.
15. The coating composition of embodiment 14 wherein z is four.
16. The coating composition of embodiment 15 comprising a mixture of silane crosslinkers where z is 3 and 4.
17. The coating composition of embodiment 15 comprising 1 to 20 weight percent of silane crosslinkers.
18. The coating composition of and of embodiments 11-16 comprising 1 to 20 wt. % of silica.
19. The coating composition of embodiment 11 comprising:
   a) 0.25 to 10 wt. % fluoroalkyl silane
   b) 0 to 20 wt. % silica
   c) 0 to 20 wt. % a silane crosslinker,
   d) 0 to 10 wt. % of an acid catalyst;
   in an organic solvent.
20. The coating composition of any of the previous embodiments further comprising 0.01 to about 10 weight percent of an acid catalyst.
21. The coating composition of embodiments 19 or 20 comprising 0.5 to 5 wt % fluoroalkylsilane.
22. The coating composition of any of embodiments 19-21 comprising 1 to 10 wt % nanoparticle silica
23. The coating composition of any of embodiments 19-21 comprising 1 to 10 wt % silane crosslinker.
24. A method of making the fluoroalkylsilane of the coating composition of any of the previous embodiments comprising the steps of hydrosilation of a fluorinated compound of the formula:

$R_f$—O—CHFCF$_2$—O—(CH$_2$)$_{q-2}$CH=CH$_2$, wherein
   $R_f$ is a perfluoroalkyl group, optionally substituted by one or more in-chain —O—, —S— or —NR$_f^1$-heteroatoms, where R$_f^1$ is a perfluoroalkyl;
   with a hydrosilane of the formula:

H—Si(X)$_x$R$_{3-x}$, wherein
   X is a hydrolysable group;
   R is a C$_1$-C$_4$ alkyl group; and
   x is 1 to 3;
   in the presence of a hydrosilation catalyst
25. The method of embodiment 24 wherein the fluorinated compound is prepared by reaction of a compound of the formula:

$R_f$—O—CF=CF$_2$ with a compound of the formula:

$$H-O-(CH_2)_{q-2}CH=CH_2,$$

in the presence of a base catalyst,
where n and $R_f$ are as previously defined,
$R_f$ is a perfluoroalkyl group, optionally substituted by one or more in-chain —O—, —S— or $NR_f^1$-heteroatoms, where $R_f^1$ is a perfluoroalkyl and q is at least 3.

26. A coated article comprising a substrate and the cured coating of any of embodiments 1-23 on a surface thereof.
27. The coated article of embodiment 26 having a receding contact angle of at least 80°, at least 90°.
28. The coated article of embodiment 27 wherein the coating is of the general formula:

$$[R_f^2SiO_{3/2}]_a[SiO_{4/2}]_b[RSiO_{3/2}]_c,$$

where
$R_f^2$ is $R_f-O-CHFCF_2-O-(CH_2)_q-$ is the unit is derived from the fluoroalkylsilane of Claim 1 where subscript "x" is 3,
$[SiO_{4/2}]$ are units derived from the crosslinking silanes having four hydrolysable groups; $[RSiO_{3/2}]$ are units derived from the crosslinking silanes having three hydrolysable groups, and subscripts a, b and c are numbers corresponding to the weight percents of each unit.
29. The coated article of any of embodiments 26-28 wherein the substrate is siliceous.

What is claimed is:
1. A coating composition comprising a fluoroalkyl silane of the formula

$$R_f-O-CHFCF_2-O-(CH_2)_q-Si(X)_xR_{3-x},$$

wherein
$R_f$ is a perfluoroalkyl group, optionally substituted by one or more in-chain —O—, —S— or $-NR_f^1-$ heteroatoms, where $R_f^1$ is a perfluoroalkyl;
X is a hydrolysable group;
R is a $C_1$-$C_4$ alkyl group;
q is at least 3; and
x is 1 to 3;
a solvent, optional acid catalyst, and silica.
2. The fluoroalkylsilane of claim 1 wherein $R_f$ is a $C_1$-$C_6$ perfluoroalkyl group.
3. The fluoroalkylsilane of claim 1 wherein q is at least 6.
4. The fluoroalkylsilane of claim 1 wherein $R_f$ is of the formula $C_nF_{2n+1}-(O-C_mF_{2m})_p-$, where n is at least 1, m is at least 2, and p may be zero or a number from 1 to 10.

5. The fluoroalkylsilane of claim 1 wherein $R_f$ is of the formula $C_nF_{2n+1}N(C_{2o}F_{2o+1})-C_mF_{2m}-$, where n is at least 1, o is at least 1 and m is at least 2.
6. The fluoroalkylsilane of claim 5 wherein each of subscripts n and m are 3 to 6.
7. The fluoroalkylsilane of claim 1 where $R_f$ is selected from $CF_3$, $C_2F_5$, $C_3F_7$ and $CF_3O(CF_2)_3$; q is 6 and greater and X is selected from Cl, $OCH_3$, $OCH_2CH_3$, $OCH_2CH_2CH_3$ and $OCH(CH_3)_2$.
8. The coating composition of claim 1 further comprising one or more silane crosslinkers of the formula:

$$Si(X^1)_zR^2_{4-z}$$

wherein each $X^1$ is independently hydroxyl, a hydrolyzable group, or a combination thereof; each $R^2$ is independently a $C_1$-$C_4$ alkyl group; z is an integer of one to four.
9. The coating composition of claim 8 wherein z is four.
10. The coating composition of claim 8 comprising a mixture of silane crosslinkers where z is 3 and 4.
11. The coating composition of claim 8 comprising 1 to 20 weight percent of silane crosslinkers.
12. The coating composition of claim 1 comprising:
a) 0.25 to 10 wt. % fluoroalkyl silane
b) 1 to 20 wt. % silica
c) 1 to 20 wt. % a silane crosslinker,
d) 0.01 to 10 wt. % of an acid catalyst;
in an organic solvent.
13. A coated article comprising a substrate and a cured coating of the coating composition of claim 1 on a surface thereof.
14. The coated article of claim 13 wherein the coating is of the general formula:

$$[R_f^2SiO_{3/2}]_a[SiO_{4/2}]_b[RSiO_{3/2}]_c,$$

where
$R_f^2$ is $R_f-O-CHFCF_2-O-(CH_2)_q-$,
$[SiO_{4/2}]$ are units derived from crosslinking silanes having four hydrolysable groups;
$[RSiO_{3/2}]$ are units derived from crosslinking silanes having three hydrolysable groups, and subscripts a, b and c are numbers corresponding to the weight percents of each unit, and each R is independently a $C_1$-$C_4$ alkyl group.
15. The coated article of claim 13 wherein the substrate is siliceous.

* * * * *

UNITED STATES PATENT AND TRADEMARK OFFICE
CERTIFICATE OF CORRECTION

PATENT NO. : 9,938,306 B2  
APPLICATION NO. : 15/023748  
DATED : April 10, 2018  
INVENTOR(S) : Zai-Ming Qiu Page 1 of 2

It is certified that error appears in the above-identified patent and that said Letters Patent is hereby corrected as shown below:

In the Specification

Column 2,  
Line 45, delete "sec" and insert -- see --, therefor.

Column 3,  
Line 31, delete "$CF_3$." and insert -- $CF_3$, --, therefor.

Column 5,  
Line 39, delete "t" and insert -- z --, therefor.

Column 6,  
Line 50, delete "u" and insert -- a --, therefor.

Column 7,  
Line 31, delete "ether," and insert -- ether; --, therefor.

Column 10,  
Line 65, delete "line;" and insert -- line: --, therefor.

Column 11,  
Line 21, delete "0313609," and insert -- 0113609, --, therefor.  
Line 45, delete "9294°" and insert -- 92-94° --, therefor.  
Line 48, delete "7578°" and insert -- 75-78° --, therefor.

Column 12,  
Line 33, delete "al" and insert -- at --, therefor.

Signed and Sealed this  
Second Day of October, 2018

Andrei Iancu  
*Director of the United States Patent and Trademark Office*

Column 16,
Line 2, delete "CBS," and insert -- CE5, --, therefor.

Column 17,
Line 31, delete "$NR_f^1$-" and insert -- —$NR_f^1$- --, therefor.

Column 18,
Line 42, after "silica" insert -- . --.
Line 62, after "catalyst" insert -- . --.

Column 19,
Line 7, delete "$NR_f^1$-" and insert -- —$NR_f^1$- --, therefor.